United States Patent [19]
Dees

[11] Patent Number: 5,344,549
[45] Date of Patent: Sep. 6, 1994

[54] OXYGEN PARTIAL PRESSURE SENSOR

[75] Inventor: Dennis W. Dees, Downers Grove, Ill.

[73] Assignee: The United States of America as represented by the United States Department of Energy, Washington, D.C.

[21] Appl. No.: 22,593

[22] Filed: Feb. 17, 1993

Related U.S. Application Data

[63] Continuation of Ser. No. 774,922, Oct. 11, 1991, abandoned.

[51] Int. Cl.$^5$ .................................... G01N 27/417
[52] U.S. Cl. ........................ 204/425; 204/424; 204/426; 204/428; 204/429
[58] Field of Search ................... 204/421–429

[56] References Cited

U.S. PATENT DOCUMENTS

| | | | |
|---|---|---|---|
| 4,152,234 | 5/1979 | Pollner | 204/427 |
| 4,276,142 | 6/1981 | Topp et al. | 204/429 |
| 4,277,323 | 7/1981 | Muller et al. | 204/426 |
| 4,505,806 | 3/1985 | Yamada | 204/426 |
| 4,879,016 | 11/1989 | Joshi | 204/427 |
| 4,947,125 | 8/1990 | De Pous | 204/424 |

Primary Examiner—T. Tung
Attorney, Agent, or Firm—Daniel D. Park; Thomas G. Anderson; William R. Moser

[57] ABSTRACT

A method for detecting oxygen partial pressure and an oxygen partial pressure sensor are provided. The method for measuring oxygen partial pressure includes contacting oxygen to a solid oxide electrolyte and measuring the subsequent change in electrical conductivity of the solid oxide electrolyte. A solid oxide electrolyte is utilized that contacts both a porous electrode and a nonporous electrode. The electrical conductivity of the solid oxide electrolyte is affected when oxygen from an exhaust stream permeates through the porous electrode to establish an equilibrium of oxygen anions in the electrolyte, thereby displacing electrons throughout the electrolyte to form an electron gradient. By adapting the two electrodes to sense a voltage potential between them, the change in electrolyte conductivity due to oxygen presence can be measured.

18 Claims, 1 Drawing Sheet

OXYGEN PARTIAL PRESSURE SENSOR

CONTRACTUAL ORIGIN OF THE INVENTION

The U.S. Government has rights in this invention pursuant to Contract Number W-31-109-ENG-38 between the U.S. Government and Argonne National Laboratory.

This is a continuation of application Ser. No. 774,922 filed Oct. 11, 1991, now abandoned.

BACKGROUND OF THE INVENTION

1. Field of the Invention

This invention relates to a method for measuring oxygen partial pressures and an oxygen partial pressure sensor and, more particularly, to detecting oxygen partial pressures by measuring the change in electronic conductance in an electrolyte that is sandwiched between an oxygen permeable electrode and an oxygen impermeable electrode.

2. Background of the Invention

The need to reduce unwanted emissions and improve fuel economy has prompted research into new oxygen sensors for internal combustion engines. The use of an exhaust-gas sensor in a feedback control arrangement allows for the regulation of the intake air-to-fuel ratio and has gained widespread use in the automobile industry.

Two types of sensors are currently utilized. The first type of sensor utilizes an oxygen pump concept and is disclosed in U.S. Pat. No. 5,010,762, and in U.S. Statutory Invention Registration No. H427. In an oxygen pump arrangement, molecular oxygen from an exhaust stream first is reduced to oxygen anions at a negatively charged, oxygen ion-porous electrode. These anions pass through the porous electrode toward another porous electrode that is positively charged. Upon reaching this second electrode, an inverse electrochemical reaction occurs whereby the oxygen anions are released as $O_2$ as they pass through the second electrode. Obviously, the utilization of two porous electrodes is crucial to any basic oxygen-pump configuration.

Another type of sensor involves comparing the subject gas with a reference gas for oxygen content. For example, U.S. Pat. No. 5,017,499 utilizes packed columns to subject fluorine gas to a halogen-lacking material to form solid fluoride and either molecular oxygen or carbon dioxide. The concentrations of the oxygen-containing compounds are then compared with a reference gas, such as air.

Another method which uses a reference gas for detecting oxygen partial pressures comprises measuring the open-circuit potential, between two porous electrodes, that is generated by the difference in the exhaust-gas oxygen partial pressure relative to a reference gas. In these arrangements, the reference gas is brought into contact with one surface of a solid electrolyte while an opposite surface of the electrolyte contacts the gas to be analyzed. The partial pressure of oxygen ($p_{O2}$) in the gas can be determined by measuring the current flowing between the electrodes situated on opposite sides of the electrolyte layer, Such a design is disclosed in U.S. Pat. No. 4,980,042. These potentiometric devices are often referred to as λ-sensors. The λ-sensor is conceptually simple and is based upon the principle that by sensing the oxygen content in an exhaust-gas stream, it is possible to approximate the engine equivalence ratio. The engine equivalence ratio is defined as follows:

$$\lambda = \frac{(\text{mass air/mass fuel})}{\text{stoichiometric (mass air/mass fuel)}} \quad \text{Eq. 1}$$

The electrode of the λ-sensor that faces the exhaust gases usually contains platinum, as platinum yields a nearly reversible oxygen electrode necessary for the open-circuit potential measurement of the λ-sensor. Also, platinum catalyzes the oxidation of gaseous species thereby lowering the oxygen partial pressure at the sensor surface relative to its exhaust-gas value. While this provides a sharp, and therefore easily distinguishable change in the λ-sensor response when the fuel mixture changes from rich to lean or from lean to rich, the disadvantage of such a catalyzed electrode surface is that the oxygen partial pressure corresponding to the λ-sensor output is lower than that of the actual exhaust-gas since the platinum electrode facilitates reaction of some of the oxygen with other exhaust gas constituents. Hence, if control of equivalence ratios away from stoichiometry is desired, the utility of the catalyzed λ-sensor is limited to sensing a deviation from the theoretical efficiency value λ without measuring the degree of such a deviation.

Generally, oxygen sensors currently used to control the intake air-to-fuel ratio of an automobile perform well near the stoichiometric air to fuel ratio but are not able to provide precise control during fuel-lean or fuel-rich operations.

Also, oxygen sensors currently in use in automobiles essentially are concentration cells with the voltage varying with the log of oxygen partial pressure. These sensors have relatively low sensitivity at elevated temperatures of 100° C. to 1000° C. Conversely, sensors that are useful at higher temperatures and particularly those for automobiles have relatively low sensitivity as to the change in the signal per change in oxygen partial pressure.

Therefore, despite a myriad of types of oxygen partial pressure sensors, a need still exists for a sensor and a method to detect oxygen partial pressures with relatively high sensitivity in widely varying fuel-rich and fuel-lean mixtures and at temperatures of 100° C. to 1000° C. as well as at temperatures above 1000° C.

SUMMARY OF THE INVENTION

It is an object of the present invention to provide a method for detecting oxygen partial pressures and an oxygen partial pressure sensor that overcomes many of the disadvantages of prior art arrangements.

It is another object of the present invention to provide a method for measuring $p_{O2}$ for use in air-to-fuel mixture determinations of combustion engines. A feature of the present method is the interposing of a solid oxide electrolyte between an oxygen-permeable electrode and an oxygen-impermeable electrode between which a voltage is applied and a current is measured. An advantage of the present invention is the ability to measure the change in current which exists in the electrolyte as a result of an electron gradient produced in the electrolyte upon exposure to oxygen which is permeating through the oxygen-permeable electrode.

Still another object of the present invention is to provide a sensitive $p_{O2}$ sensor for use in automobile combustion applications. A feature of the invention is its built-in signal amplifier design whereby the amount of current produced in response to the oxygen concentration can be controlled by the applied potential. An advantage of the invention is an increase signal response for a wide spectrum of air-to-fuel mixtures.

Yet another object of the present invention is to provide an $p_{O2}$ sensor that can be used at elevated temperatures. A feature of the present invention is incorporating a solid oxide material as an electrolyte whose electronic conductivity will vary with the oxygen partial pressure. An advantage of the present invention is providing a sensor with higher sensitivity and wider range of operation at temperatures of 100° C. to 1000° C. as well as at temperatures above 1000° C.

A further object of the present invention is to provide a device and method to enhance sensitivity to oxygen partial pressures of automobile exhaust emissions for a wide range of air-to-fuel mixtures.

In brief, the objects and advantages of the present invention are achieved by an oxygen partial pressure sensor and a method of detecting oxygen partial pressures. A solid electrolyte having a first surface and a second surface is interposed between a porous or oxygen-permeable electrode and a nonporous or oxygen-impermeable electrode. The first surface of the solid electrolyte contacts an electrolyte side of a porous electrode and the second surface of the solid electrolyte contacts the nonporous electrode. The electrical conductivity of the solid electrolyte is affected when oxygen from oxygen laden gas contacting the exhaust stream side of the porous electrode permeates through the electrode to the electrolyte side of the porous electrode and contacts the first surface of the electrolyte to establish an equilibrium of oxygen anions in the electrolyte, thereby displacing electrons throughout the electrolyte to form an electron gradient. By adapting the two electrodes to sense a voltage potential between them, the change in electrolyte conductivity due to oxygen partial pressure can be measured.

The invention teaches a method for measuring oxygen partial pressure comprising contacting oxygen to a solid oxide electrolyte and measuring the subsequent electrical conductivity of the solid oxide electrolyte.

BRIEF DESCRIPTION OF THE DRAWING

The present invention together with the above and other objects and advantages may best be understood from the following detailed description of the embodiment of the invention illustrated in the drawings, wherein.

DETAILED DESCRIPTION OF THE PREFERRED EMBODIMENT

Figure 1:
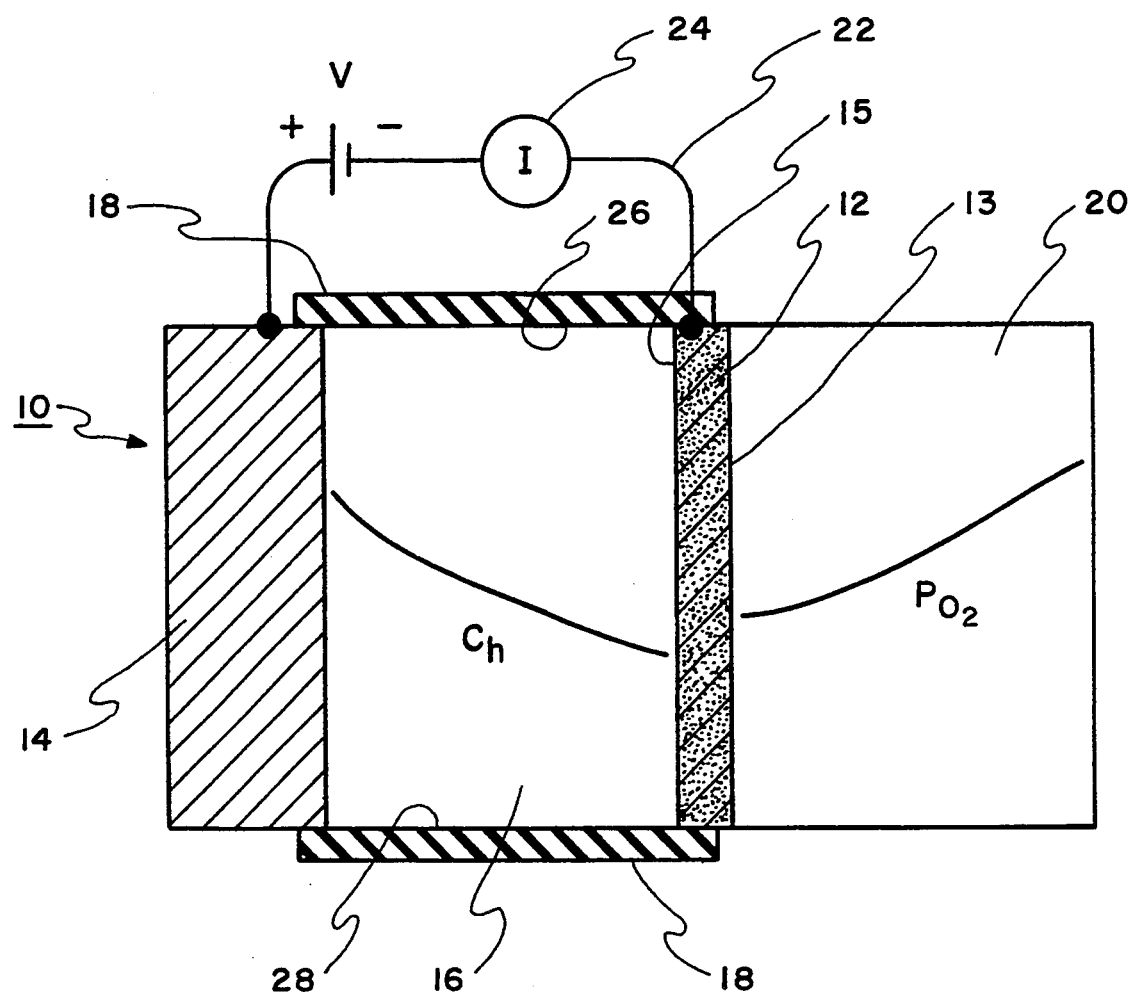
FIG. 1 is a diagram of an exemplary sensor illustrating the present invention.

The invention described herein is much more sensitive to changes in oxygen partial pressure than the more common oxygen pump or open circuit type sensors described above. The invented method and device operates by exploiting the sensitivity of a solid electrolyte to oxygen partial pressures, but without relying on oxygen transport through the electrolyte. Instead, $p_{O2}$ is measured by the effect it has on the electronic conductance of a specific electrolyte. This effect is depicted in Equation 2, below:

$$\tfrac{1}{2}O_2 + V_o \rightleftharpoons O_o x + 2h+ \qquad \text{Eq. 2}$$

wherein $V_o$ is a vacancy at an oxygen ion site in the lattice of the electrolyte, $O_o x$ is an oxygen ion at an oxygen site, and $h+$ is a hole. Equation 2 shows that the exposure of exhaust oxygen gas to the first surface of the solid electrolyte establishes an equilibrium of oxygen anions in the electrolyte and the exhaust gas. A cascade effect occurs whereby an oxygen vacancy $V_o$ in the lattice of the electrolyte becomes filled with an oxygen anion, thereby displacing the two holes that resided there. These two holes then displace two electrons, which in turn displace two more holes. This cascade manifests itself as an electron gradient across the electrolyte that is determined by the nature of the electrolyte. This gradient establishes the electrolyte's conductivity. When a voltage is applied across the electrolyte, a current flows that is a function of the conductivity of the electrolyte. In essence, the invention is a classical application of Ohm's Law, represented by $V=IR$, wherein the sensor 10 is fixed at a certain voltage, V, such as 0.25 V, and resistance, R, is a function of the $p_{O2}$, thereby making the current, I, a function of the $p_{O2}$.

Referring to FIG. 1, there is shown a device or sensor for detecting oxygen partial pressures at temperatures from about 100° C. to above 1000° C. generally designated by the reference numeral 10. Oxygen partial pressure sensor 10 includes a porous electrode 12, having an exhaust stream side 13 and an electrolyte side 15, with a nonporous, blocking electrode 14 for blocking the transport of oxygen anions with a solid electrolyte 16 interposed between the two electrodes 12 and 14.

Insulating members 18 could be utilized to isolate the third surface 26 and fourth surface 28 of the solid electrolyte from ambient oxygen by mechanically connecting the peripheral edges of the porous electrode 12 with the peripheral edges of the nonporous electrode 14. The insulator 18 must be nonporous and electrically nonconductive. However, the need for an insulator can be eliminated by increasing the aspect ratio of the sensor 10 by making the electrolyte 16 very thin compared to its overall length.

In operation, the voltage across the electrodes, applied with any standard conducting material, such as metallic wire 22, is adjusted such that the current does not alter the equilibrium of oxygen at the electrodes. The applied voltage will vary with the type of electrolyte used, but then will be maintained at a specific value so that Ohm's law can be used to determine $P_{O2}$. Generally, the current can be measured using an ammeter 24 within a circuit defined by a conductor 22 coupling the porous electrode 12 to the cathode of an external voltage source V and coupling the nonporous blocking electrode 14 to the anode of the external voltage source V.

The Solid Oxide Electrolyte

Many solid oxide ceramics exhibit electronic conductivities that vary with the partial pressure of oxygen. A variety of oxide ceramics can be used as the electrolyte 16 in the oxygen partial pressure sensor 10. Doped metal oxides with a fluorite structure, such as $ZrO_2$, $ThO_2$, $CeO_2$, and $HfO_2$, are suitable choices. Dopants can be added to these ceramic oxides for an even more varied response to oxygen. Dopants are also used to stabilize a phase, so that, for example, a solid electrolyte will not change phases over the operating range. Dopant possibilities include calcium, yttrium, lanthanum, and magnesium. Yttrium is typically added to zirconium-containing electrolytes in oxygen-pump configurations for enhanced oxygen-anion conducting capabilities.

Thicknesses, L, of the electrolyte 16 will vary depending on the fabrication method used to deposit the electrolyte 16 layer onto the porous 12 and nonporous 14 electrodes. Generally, however, a value of about 0.01 μm is an acceptable minimum thickness. Maximum thicknesses will vary with the material used and the device's time constant requirements. A value of 100 μm is a good maximum thickness value.

Equations 3 and 4, below, describe the variation of the concentration of electrons and holes at the gas/solid oxide first surface interface:

$$\tfrac{1}{2}O_2(gas) + V_0 + 2e^- \rightleftharpoons O_o^x \quad \text{and} \qquad \text{Eq. 3}$$

$$\tfrac{1}{2}O_2(gas) + V_0 \rightleftharpoons O_o^x + 2h^+ \qquad \text{Eq. 4}$$

where $V_o$ is a vacancy at an oxygen ion site, $O_o x$ is an oxygen ion at an oxygen ion site, $e^-$ is an electron, and $h^+$ is a hole.

The current density (I) for oxides, where the vacancy concentration is set by the dopant level and equilibrium has been established, is given by the following equation:

$$I = (RT)/(FL) \{\sigma_h[1 - \exp(-(EF)/(RT))] + \sigma_e[\exp((EF)/(RT)) - 1]\} \qquad \text{Eq. 5}$$

where L is the thickness of the electrolyte and $\sigma_e$ and $\sigma_h$ are the electron and hole conductivities adjacent to the porous electrode, respectively. Equations 6 and 7 illustrate how the two conductivities are related to the $p_{O2}$:

$$\sigma_e = \sigma^o{}_e(p_{O2})^{-\tfrac{1}{4}} \qquad \text{Eq. 6}$$

$$\sigma_h = \sigma^o{}_h(p_{O2})^{+\tfrac{1}{4}} \qquad \text{Eq. 7.}$$

where $\sigma^o{}_e$ and $\sigma^o{}_h$ are the conductivities of electrons and holes at one atmosphere, respectively. Equations 6 and 7 illustrate that when the voltage across the electrodes is held constant, the current through the electrolyte varies with the one-quarter power of the oxygen partial pressure. The oxide ceramic does not have to be doped to be an oxygen sensor. In that case the concentration of vacancies is not constant and the relationship between the current and the oxygen partial pressure cannot be expressed in a closed analytical form. However, it can be determined either numerically or experimentally.

Porous Electrode

Generally, two types of electrodes are utilized in the preferred embodiment of the invention. One is porous electrode 12, i.e, an oxygen-conductor, and the other is a dense, nonporous electrode 14, and therefore not an oxygen conductor. This nonporous electrode 14 is the blocking electrode.

For simplicity, the electrical conductivity of the electrodes 12 and 14 should not depend on the oxygen partial pressure and should be much greater than the electrical conductivity of the electrolyte 16. Furthermore, the type of material used to formulate the porous electrode 12 will vary with the application of the oxygen sensor 10. The electrode material must be stable in reducing (fuel) and oxidizing (air) environments, and also thermally stable up to maximum operating temperature. Any metal (e.g. platinum) or doped metal oxide that is compatible and adheres to the electrolyte 16 can be used. As a primary objective of the instant invention 10 is to provide enhanced $P_{O2}$ measurements away from stoichiometry, decatalyzed platinum electrodes, such as lead-poisoned platinum electrodes, could be utilized. For example, whereas a catalyzed electrode causes some of the oxygen in the exhaust gas to react with other gas constituents, therefore lowering the actual $p_{O2}$ value, decatalyzed electrodes allow oxygen to permeate unscathed.

The thickness of the porous electrode 12 can vary, but generally any thickness must accommodate the rapid transport of exhaust gases. The porous electrode 12 may also include a protective coating 20 on the exhaust side 13 of the porous electrode 12, and the thickness of this protective coating 20 must be considered when determining gas flow rates. Generally, such protective coatings 20 can be any metal oxide that is porous, stable, adherent and compatible with the porous electrode 12. A class of compounds currently used as protective coatings are the spinels, which is a class of metal oxide compounds having the following general formula:

$$M''M_2'''O_4$$

wherein M'' is magnesium, zinc, manganese, or ferrous iron and M''' is aluminum, chromium, ferric iron, or manganese. These compounds characteristically have a high hardness and refractive index. Some examples include gaehnite, $ZnAl_2O_4$; franklinite (Fe, Zn, Mn) $Fe_2O_4$; and chromite $FeCr_2O_4$.

The thickness of the porous electrode 12 should be thin compared to the spinel coating thickness. Generally, porous electrode thicknesses must be less than 0.2 times the thickness of the spinel coating. The thickness of the protective coating 20 is determined by the fabrication technique and the environment in which the device 10 is to be operated. A minimum thickness should approximate 10 microns (μm). The maximum thickness is determined by the effective diffusivity of the layer and the required reaction time of the device. FIG. 1 depicts relative hole concentrations $C_h$ and $p_{O2}$ profiles for the solid electrolyte 16 and spinel coating regions, respectively after a sudden change in $p_{O2}$. An exemplary protective coating 20 thickness of about 1000 μm will provide appropriate protection from exhaust gases.

Blocking Electrode

As the function of the blocking electrode 14 is to allow electrons or holes to pass into the blocking electrode 14 while blocking the flow of other ionic species, any current density measured at the blocking electrode 14 is due solely to the conduction of electrons and holes. Blocking electrodes previously have been employed so as to evaluate the transport properties of electrons and holes in solid electrolytes which also conduct other ionic species. (See, for example J. Electrochem. Soc. 114:752-8, 1967.)

The blocking electrode 14 can be comprised of suitable material that adheres to the solid electrolyte 16 while making a dense coating. Some constituents of blocking electrode 14 may include ceramic, metal, or some electronically conductive, thermally resilient material that can withstand multiple cycling from room temperature to more than 800° C., and then back down to room temperature again. As with porous electrode 12 constituents, blocking electrode 14 materials should withstand the maximum operating temperature. Any metal that is compatible with the solid electrolyte 16, adheres to the solid electrolyte 16, is stable in high temperature oxidizing and reducing situations, and that is electronically conductive, can be used. Exemplary materials include metals, such as platinum, and doped metal oxide, such as La(Mg)MnO$_3$.

If the blocking electrode 14 has the above properties, then any thickness is acceptable.

Sensor Fabrication

The operation of the sensor 10 depends on the relative thicknesses of the layers of material which comprise the device. Generally, the thicknesses of the layers should accommodate a 100 millisecond response time to any changes in the exhaust stream constituents. Fabrication of the device can take a variety of forms, depending on the layer deposition technique or techniques used. One method can begin with a rigid substrate, perhaps a material that would also serve as the blocking electrode 14 layer, onto which the solid electrolyte 16 layer, porous electrode 12 layer, and protective coating 20 layer could be deposited. Exemplary deposition techniques include the following:

screen printing,
chemical vapor deposition,
physical vapor deposition,
tape casting,
spray coating, and
curtain coating.

This list of deposition techniques is not meant to be exhaustive, but merely representative of the methods use to apply closely regulated, thin films.

Sensor Operation

In operation, the voltage across the electrodes is adjusted such that the current does not alter the equilibrium at the electrodes and can still be easily measured. The thickness and type of the oxide ceramic electrolyte 16 can be adjusted so that the time constant of the sensor 10 is limited by the time constant of the equilibrium reaction. Through an order of magnitude estimate, the time constant of electrolyte can be shown to be approximately $L^2/D$, where D is the diffusion coefficient of the electrons or holes, and L is the thickness of the oxide electrolyte 16 between the two electrodes. If the sensor 10 is used to control at a set point then equilibrium would not necessarily have to be established.

An important question to be answered for new oxygen-sensor designs is the unit's response time, with a steady-state response within about 100 milliseconds as desirable. The thicknesses of the solid electrolyte 16 layer, the porous electrode 12, and the protective coating 20 layer on the exhaust-exposed 13 surface of the porous electrode 12 determine the current response of the sensor 10. As noted above, the porous electrode 12 is extremely thin relative to the solid oxide electrolyte 16 and protective coating 20.

The length, relative to the thickness of the electrolyte 16 and porous electrode 12 layers also effects the conductivity of the electrolyte 16. This is due to the third surface 26 and forth surface 28 of the electrolyte 16, which are perpendicular to the planes containing the electrodes, being exposed to the $p_{O2}$ from ambient air or the exhaust stream, thereby leading to unaccounted for changes in the conductance characteristics of the electrolyte 16. These edge effects are particularly notable in devices having shorter lengths, relative to the thickness L of the device 10 and are not seen in longer, thinner configurations. To eliminate these edge effects, insulators 18 can be positioned so as to isolate the electrolyte 16 from nonexhaust sources of oxygen. Conversely, the need for insulators 18 can be eliminated by increasing the aspect ratio of the sensor by making the electrolyte 16 layer very thin compared to its overall length.

The invented sensor 10 is much more sensitive to changes in oxygen partial pressure than the more common method of monitoring the oxygen partial pressure with a concentration cell. The flexibility of various sensitivity is somewhat reduced in the narrow region where the electron and hole conductivity are of the same order of magnitude, but because of the many oxide ceramics that exhibit an electronic conductivity dependant on oxygen partial pressure, and the numerous dopants that can be added to the base material, the flexibility for various oxygen sensor applications is great.

While the invention has been described with reference to details of the illustrated embodiment, these details are not intended to limit the scope of the invention as defined in the appended claims.

The embodiment of the invention in which an exclusive property or privilege is claimed is defined as follows:

1. An oxygen partial pressure sensor comprising:
   a solid electrolyte having a first surface and a second surface;
   an oxygen permeable porous electrode, acting as a cathode, having an exhaust stream side and an electrolyte side, wherein the electrolyte side of said oxygen permeable porous electrode contacts the first surface of said solid electrolyte and entirely covers mid first surface;
   an oxygen impermeable nonporous electrode, acting as an anode, contacting the second surface of said solid electrolyte and entirely covering said second surface;
   oxygen impermeable insulator means cooperating with said oxygen permeable porous electrode and said oxygen impermeable nonporous electrode and surrounding said solid electrolyte so as to allow essentially only the first surface of said solid electrolyte contacting said oxygen permeable porous electrode to be exposed to an exhaust stream such that a flow of oxygen ions through the solid electrolyte is essentially blocked;
   means for applying a voltage across said electrodes; and
   means for sensing a flow of current between said electrodes.

2. An oxygen partial pressure sensor as recited in claim 1 wherein said solid electrolyte is a ceramic oxide.

3. An oxygen partial pressure sensor as recited in claim 2 wherein said ceramic oxide is selected from the group consisting of $ZrO_2$, $ThO_2$, $CeO_2$, $HfO_2$ and combinations thereof.

4. An oxygen partial pressure sensor as recited in claim 1 wherein said electrolyte has a minimum thickness of about 0.01 $\mu m$ and a maximum thickness of about 100 $\mu m$.

5. An oxygen partial pressure sensor as recited in claim 1 wherein said exhaust stream side of said oxygen permeable porous electrode is coated with a spinel compound.

6. An oxygen partial pressure sensor as recited in claim 5 wherein the thickness of said spinel compound is between approximately 10 μm and 100 μm.

7. An oxygen partial pressure sensor as recited in claim 5 wherein said spinel compound has the following general formula:

$$M''M_2'''O_4$$

wherein M'' is magnesium, zinc, manganese, or ferrous iron and M''' is aluminum, chromium, ferric iron, or manganese.

8. An oxygen partial pressure sensor as recited in claim 5 wherein the thickness of said oxygen permeable porous electrode is less than 0.2 times the thickness of the spinel coating.

9. An oxygen partial pressure sensor as recited in claim 1 wherein said means for applying a voltage across said electrodes is maintained at a specific voltage.

10. An oxygen partial pressure sensor comprising:
a substantially flat solid electrolyte having a first and a second surface;
an oxygen permeable porous electrode, acting as a cathode, having an exhaust stream side and an electrolyte side, wherein the electrolyte side of said oxygen permeable porous electrode contacts the first surface of said solid electrolyte;
an oxygen impermeable nonporous electrode, acting as an anode, contacting the second surface of said solid electrolyte;
means for applying a voltage across said electrodes; and
means for sensing a flow of current between said electrodes;
wherein said oxygen permeable porous electrode covers the entire first surface of said solid electrolyte;
wherein said oxygen impermeable nonporous electrode covers the entire second surface of said solid electrolyte; and
wherein said solid electrolyte is thin so as to allow essentially only the first surface of said solid electrolyte to be exposed to an exhaust stream;
such that a flow of oxygen ions through the solid electrolyte is essentially blocked.

11. An oxygen partial pressure sensor as recited in claim 10 wherein said solid electrolyte is a ceramic oxide.

12. An oxygen partial pressure sensor as recited in claim 10 wherein said ceramic oxide is selected from the group consisting of $ZrO_2$, $ThO_2$, $CeO_2$, $HfO_2$ and combinations thereof.

13. An oxygen partial pressure sensor as recited in claim 10 wherein said solid electrolyte has a minimum thickness of about 0.01 μm and a maximum thickness of about 100 μm.

14. An oxygen partial pressure sensor as recited in claim 10 wherein said exhaust stream side of said oxygen permeable porous electrode is coated with a spinel compound.

15. An oxygen partial pressure sensor as recited in claim 14 wherein the thickness of said spinel compound is between approximately 10 μm and 1000 μm.

16. An oxygen partial pressure sensor as recited in claim 14 wherein said spinel compound has the following general formula:

$$M''M_2'''O_4$$

wherein M'' is magnesium, zinc, manganese, or ferrous iron and M''' is aluminum, chromium, ferric iron, or manganese.

17. An oxygen partial pressure sensor as recited in claim 14 wherein the thickness of said oxygen permeable porous electrode is less than 0.2 times the thickness of the spinel coating.

18. An oxygen partial pressure sensor as recited in claim 14 wherein said means for applying a voltage across said electrodes is maintained at a specific voltage.

* * * * *